United States Patent
Li et al.

(10) Patent No.: US 7,649,973 B1
(45) Date of Patent: Jan. 19, 2010

(54) APPARATUS AND METHOD FOR Z-LOCATION DEPENDENT X-RAY BEAM FILTRATION FOR IMAGING SYSTEM

(75) Inventors: Baojun Li, Waukesha, WI (US); Thomas Louis Toth, Brookfield, WI (US); Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/244,569

(22) Filed: Oct. 2, 2008

(51) Int. Cl.
*G01N 23/083* (2006.01)
(52) U.S. Cl. .............................. 378/9; 378/16
(58) Field of Classification Search ............ 378/4, 378/9, 156, 5, 16, 158, 159
See application file for complete search history.

(56) References Cited

U.S. PATENT DOCUMENTS

| | | | |
|---|---|---|---|
| 5,625,661 A | 4/1997 | Oikawa | |
| 6,968,042 B2 | 11/2005 | Toth et al. | |
| 7,305,063 B2 | 12/2007 | Heuscher | |
| 7,430,282 B2 | 9/2008 | Mori et al. | |
| 2005/0031084 A1* | 2/2005 | Toth et al. | 378/156 |
| 2006/0285633 A1* | 12/2006 | Sukovic et al. | 378/9 |

FOREIGN PATENT DOCUMENTS

WO   WO 2008/024586 A2   2/2008

OTHER PUBLICATIONS

Shinichiro Mori et al., Prototype heel effect compensation filter for cone-beam CT, Institute of Physics Publishing, Phys. Med. Biol. 50 (2005) N359-N370, doi: 10.1088/0031-9155/50/22/N02 (12) pgs.

* cited by examiner

*Primary Examiner*—Hoon Song
(74) *Attorney, Agent, or Firm*—Dean D. Small; The Small Patent Law Group

(57) ABSTRACT

An imaging system includes at least two x-ray sources, an x-ray detector assembly and an attenuation filter. The at least two x-ray sources are displaced along a z-axis and configured to alternately emit x-ray beams. The x-ray detector assembly is configured to detect the x-ray beams. The attenuation filter is mounted proximate the at least two x-ray sources and is configured to provide different amounts of x-ray attenuation to the x-ray beams along the z-axis.

20 Claims, 6 Drawing Sheets

APPARATUS AND METHOD FOR Z-LOCATION DEPENDENT X-RAY BEAM FILTRATION FOR IMAGING SYSTEM

BACKGROUND OF THE INVENTION

This invention relates generally to a computed tomography (CT) system and more particularly to systems and methods for eliminating artifacts caused when using multiple x-ray sources.

Typically, in a CT system, an x-ray tube emits a fan-shaped x-ray beam or a cone-shaped x-ray beam toward a subject or object positioned on a table. The beam, after being attenuated by the subject, impinges upon a detector assembly. The intensity of the attenuated x-ray beam received at the detector assembly is typically dependent upon the attenuation of the x-ray beam by the subject. Each detector element of the detector assembly produces a separate electrical signal indicative of the attenuated x-ray beam received.

In known third generation CT systems, the x-ray source and the detector assembly are rotated on a gantry around the object to be imaged so that a gantry angle at which the fan-shaped or cone-shaped x-ray beam intersects the object constantly changes. The table supporting the subject may be advanced while the gantry is rotating around the object being imaged. Data representing the strength of the received x-ray beam at each of the detector elements is collected across a range of gantry angles. The data is ultimately reconstructed to form an image of the object.

It is advantageous to have large coverage in a z-direction for certain procedures. For example, large coverage allows for the collection of data in fewer gantry revolutions, which leads to a quicker acquisition time. Also, large coverage may allow an entire organ to be acquired in a single gantry revolution. The size of the coverage may be increased in the z-direction by increasing the width of the detector assembly. To overcome limitations caused by a cone-beam artifact for wide detector assemblies that use a single x-ray source, two or more x-ray sources may be displaced along the z-axis. When imaging, the x-ray sources alternately transmit x-rays. The x-ray beams from the x-ray sources may partially overlap each other when traveling through the subject, and therefore the x-ray flux varies along the z-axis. The combined image experiences noise artifacts due to the greater flux within the overlapping region. In addition, the patient is exposed to approximately twice the level of radiation within the overlapping region as compared to non-overlapping regions.

BRIEF DESCRIPTION OF THE INVENTION

In one embodiment, an imaging system includes at least two x-ray sources, an x-ray detector assembly and an attenuation filter. The at least two x-ray sources are displaced along a z-axis and configured to alternately emit x-ray beams. The x-ray detector assembly is configured to detect the x-ray beams. The attenuation filter is mounted proximate the at least two x-ray sources and is configured to provide different amounts of x-ray attenuation to the x-ray beams along the z-axis.

In another embodiment, a method for at least partially compensating for increased x-ray flux due to multiple x-ray sources mounted along a z-axis includes transmitting x-ray beams alternately from at least two adjacent x-ray sources. The x-ray beams form an overlapping region within an imaging area. An attenuation filter is positioned between the at least two adjacent x-ray sources and an x-ray detector assembly, and provides different amounts of x-ray attenuation to the x-ray beams along the z-axis.

In yet another embodiment, a computed tomography (CT) imaging system includes at least two x-ray sources aligned along a z-axis, a detector assembly and an attenuation filter. The detector assembly is positioned to detect x-rays beams from the at least two x-ray sources, wherein the at least two x-ray sources are configured to alternately emit x-ray beams that partially overlap within an overlapping region of an imaging area that is located between the at least two x-ray sources and the detector assembly. The attenuation filter is positioned between the at least two x-ray sources and the imaging area, and is configured to provide relatively higher x-ray attenuation along the z-axis corresponding to the overlapping region and relatively lower x-ray attenuation along the z-axis corresponding to at least one non-overlapping region of the imaging area.

DETAILED DESCRIPTION OF THE INVENTION

Figure 1:
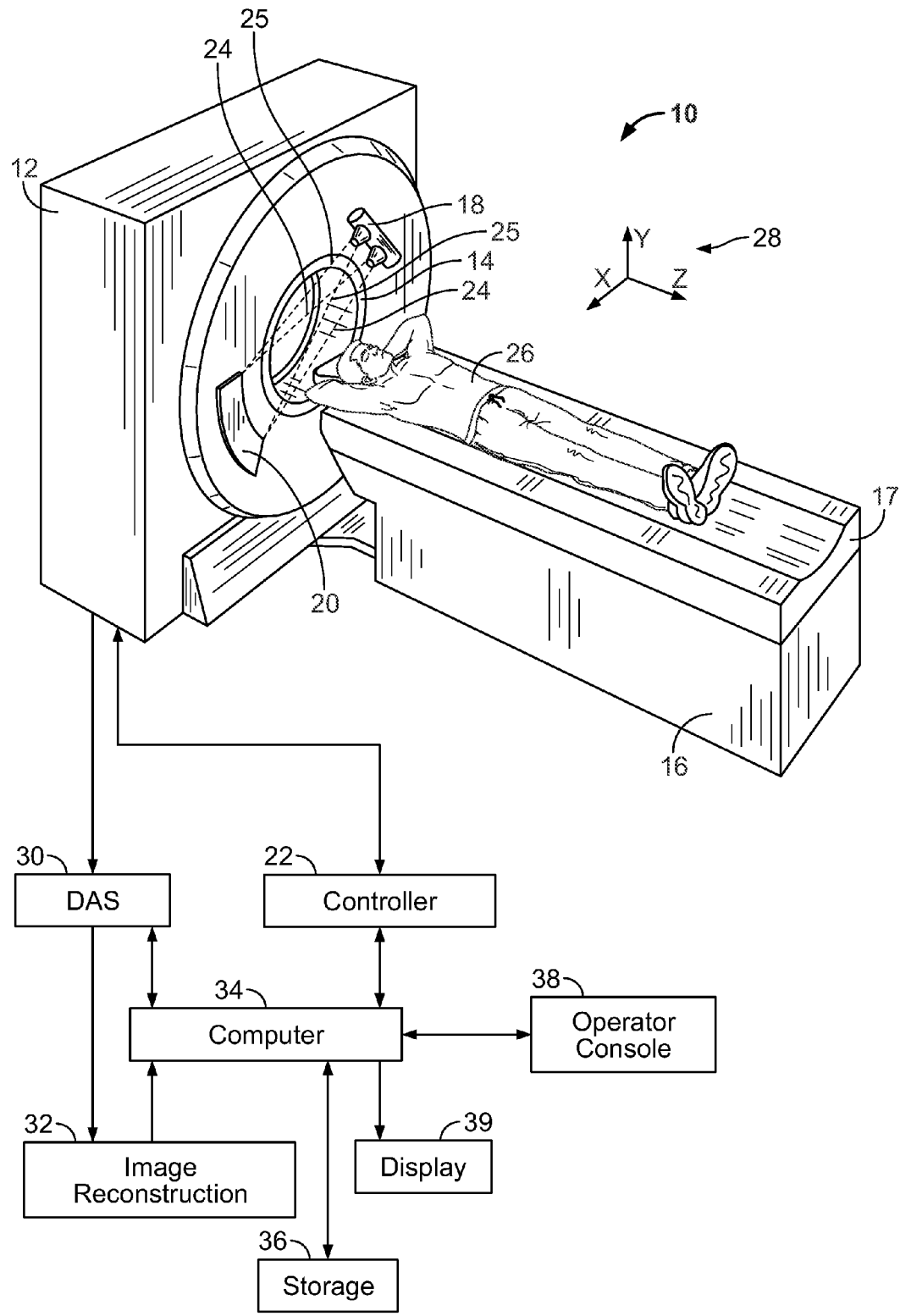
FIG. 1 is a schematic representation of a computed tomography (CT) system formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 is a schematic representation of a computed tomography (CT) system 10 according to an embodiment of the present invention. The CT system 10 includes a gantry support 12, a gantry 14, a table 16, a moveable table portion 17, an x-ray tube 18, a two-dimensional detector assembly 20 that has an x-ray sensitive surface, and a controller 22. The gantry 14 is configured to rotate within the gantry support 12. The gantry 14 is adapted to retain and support the x-ray tube 18 and the detector assembly 20. The x-ray tube 18 is configured to emit at least a first x-ray beam 24 and a second x-ray beam 25 towards the detector assembly 20. The detector assembly 20 comprises a plurality of detector elements (not shown). Each of the plurality of detector elements produces an electrical signal that varies based on the intensity of the first or second x-ray beam 24, 25 received during a sampling interval. The table 16 is configured to support an object or subject 26 being scanned. The moveable table portion 17 is capable of translating the subject 26 in a z-direction with respect to the gantry 14 as indicated by a coordinate axis 28. The controller 22 is configured to control the rotation of the gantry 14, the translation of the moveable table portion 17, and the activation of the x-ray tube 18.

A data acquisition system (DAS) 30 may sample data from the detector elements within the detector assembly 20 and, if necessary, converts the data to digital signals for subsequent processing. An image reconstructor 32 receives sampled and digitized x-ray data from the DAS 30 and performs high-speed image reconstruction. For example, signals associated with scan data from the first and second x-ray beams 24 and 25 may be processed and ultimately combined into a single reconstructed image. The reconstructed image is applied as an input to a computer 34 or other processor, which may store the image in a storage device 36. In one embodiment, the image reconstructor 32 may be one or more hardware, firmware or software modules executing on the computer 34.

The computer 34 also receives commands and scanning parameters from an operator via operator console 38 that may have a keyboard as well as other input devices. A display 39 allows the operator to observe the reconstructed image(s) and other data from the computer 34.

The term computer as used herein is not limited to only those integrated circuits referred to in the art as computers, but broadly refers to computers, processors, microprocessors, microcomputers, programmable logic controllers, application specific integrated circuits, and other programmable circuits. Also, although at least some of the embodiments described herein are described in a medical setting, it is contemplated that the benefits of at least one embodiment apply to non-medical imaging systems as well, such as those systems typically employed in an industrial setting or a transportation setting, such as, for example, a baggage scanning system for an airport or other transportation center.

Figure 2:
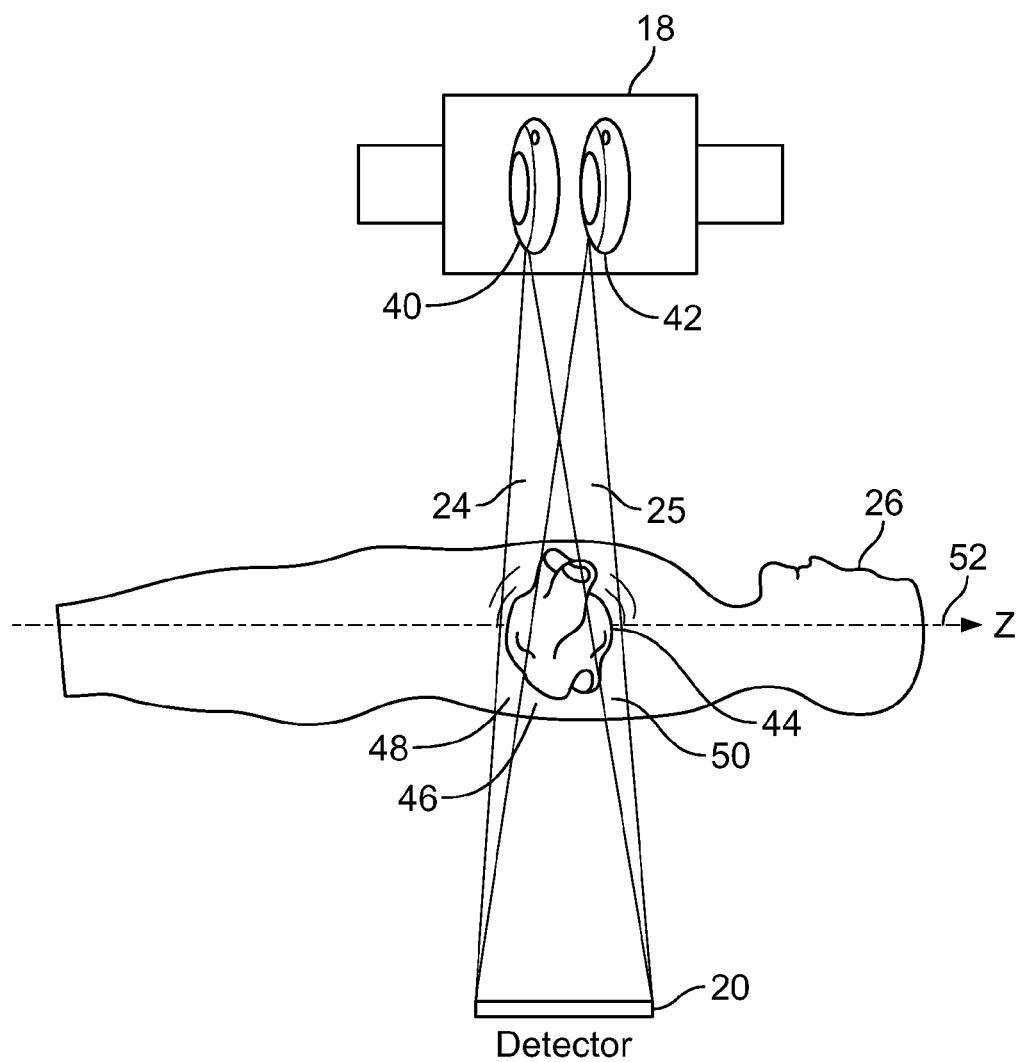
FIG. 2 illustrates an example of using the CT system of FIG. 1 to image an organ within a subject in accordance with an embodiment of the present invention.

FIG. 2 illustrates an example of using the CT system 10 of FIG. 1 to image an organ within the subject 26. The x-ray tube 18 is illustrated as having first and second anodes 40 and 42. The first and second anodes 40 and 42 (or other x-ray beam sources) are displaced or distributed along a z-axis 52. The first and second anodes 40 and 42 alternately produce the first and second x-ray beams 24 and 25. The x-ray tube 18 may be configured with other apparatus and/or means to generate the first and second x-ray beams 24 and 25. A single electron source (not shown) may be used to generate both of the x-ray beams 24 and 25, or multiple electron sources may be used, such as one electron source for each of the anodes 40 and 42. Additionally, the x-ray tube 18 may be configured to produce more than two x-ray beams, such as by having three or more anodes. For example, the x-ray tube 18 or other source generator may generate three, four or more x-ray beams dispersed along the z-axis 52. In one embodiment, more than two sources may produce more than two x-ray beams that partially overlap with respect to each other.

In FIG. 2, the anatomy 44 of interest being imaged is the heart (enlarged in FIG. 2 for illustrative purposes). The first and second x-ray beams 24 and 25 together form the field-of-view and illustrate the coverage along the z-axis 52. The first and second x-ray beams 24 and 25 each pass through a portion of the anatomy 44 and form an overlapping region 46 where the x-ray beams 24 and 25 both pass through the same portion of the anatomy 44 or field-of-view. Non-overlapping regions 48 and 50 indicate portions of the anatomy 44 wherein only one of the first and second x-ray beams 24 and 25 passes through the anatomy 44. As discussed before, the DAS 30 (as shown in FIG. 1) receives image or projection data associated with each of the alternating x-ray beams 24 and 25. The image reconstructor 32 and computer 34 combine the multiple sets, such as two or more sets, of projection data into a reconstructed image. The noise level in the non-overlapping regions 48 and 50 is higher than the noise level in the overlapping region 46 because the overlapping region 46 receives twice as much x-ray flux than the non-overlapping regions 48 and 50. In one example, the noise level in the non-overlapping regions 48 and 50 is approximately 40-45 percent higher than the noise level in the overlapping region 46. The high level of noise variation across the reconstructed image causes image qualities issues, such as, but not limited to, banding in multi-plane reformat images.

Methods and apparatus are now described to at least partially compensate for the increased x-ray flux within the overlapping region 46 by balancing the radiation intensity along the z-axis 52 of the first and second x-ray beams 24 and 25 emitted to the detector assembly 20. In at least one embodiment, a compensation or attenuation filter that increases attenuation of the x-ray beams 24 and 25 within the overlapping region 46 along the z-axis 52 is used.

Figure 3:
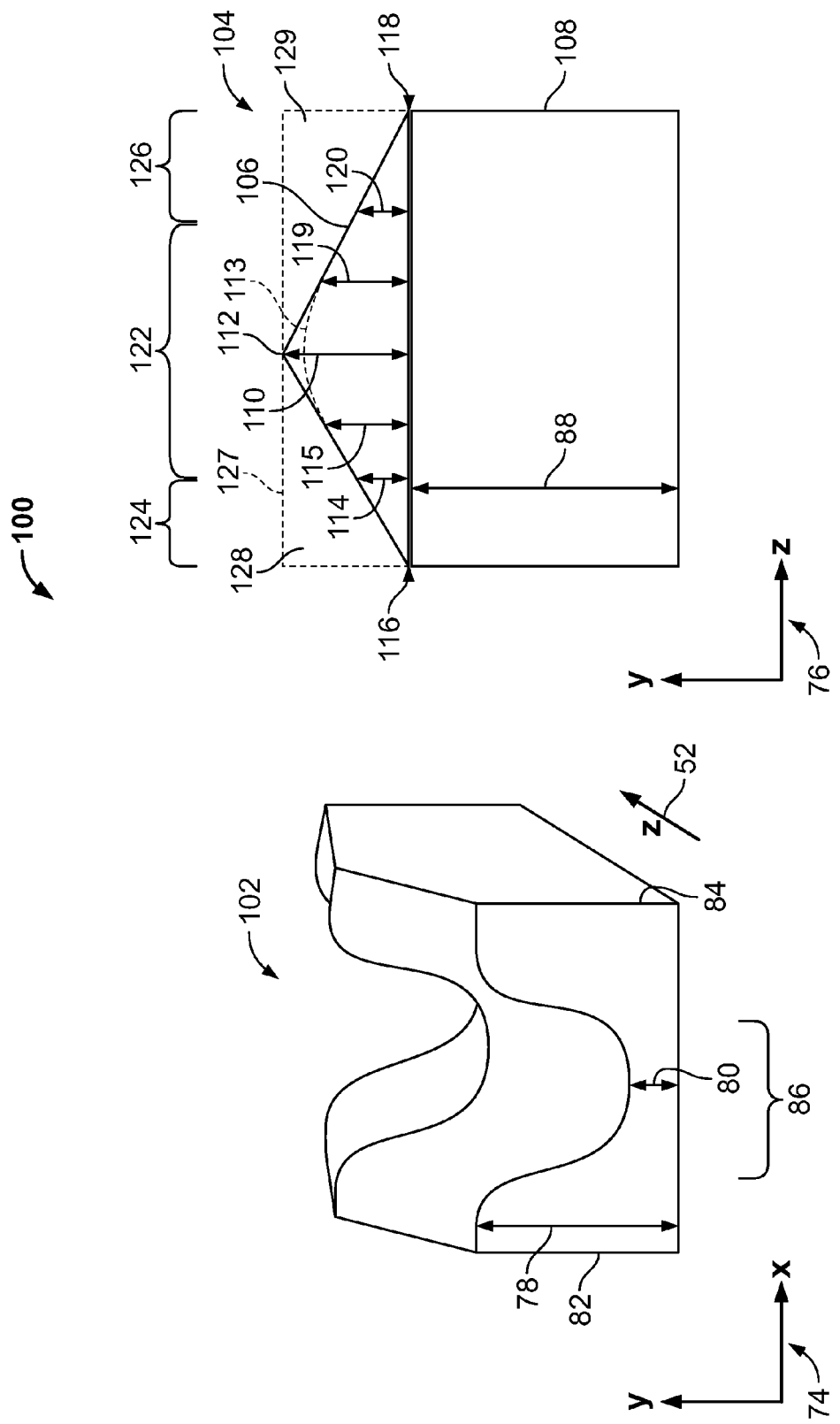
FIG. 3 illustrates an attenuation filter in both a perspective view and a side view along the y-z plane in accordance with an embodiment of the present invention.

FIG. 3 illustrates an attenuation filter 100 in both a perspective view 102 and a side view 104 as viewed along a y-z plane 76 in accordance with an embodiment of the present invention. The attenuation filter 100 provides different attenuation across the z-axis 52 to the first and second x-ray beams 24 and 25 depending upon the z-location. Referring to the perspective view 102, in one embodiment the attenuation filter 100 is substantially "U" shaped within an x-y plane 74, providing different attenuation across the x-axis. A thickness 78 of x-ray attenuating material is thicker at outer edges 82 and 84 to provide a greater level of x-ray attenuation than thickness 80 within a central portion 86 of the attenuation filter 100. The "U" shape of the attenuation filter 100 in the x-y plane 74 provides beam hardening correction and minimizes the x-ray exposure to peripheral areas of the subject 26. It should be understood that other shapes may be used to attenuate the x-ray beams differently across the x-axis, including providing a constant level of attenuation across the x-axis. Turning to the side view 104, a triangular shaped portion 106 is illustrated with rectangular shaped portion 108 that represents a constant thickness 88 corresponding to the thicknesses 78 and 80 in the x-y plane 74. The triangular shaped portion 106 has a thickness 110 at a peak 112 that is greater than thicknesses 115 and 119, while thicknesses 115 and 119 are greater than thicknesses 114 and 120, which are closer to outer edges 116 and 118 along the z-axis 52.

As used herein, the term "triangular shaped" is defined as a shape including a top having two portions and a bottom, wherein the top has at least one peak 112 and wherein the two portions extending from the peak 112 may be at equal angles from a vertical tangent extending from the peak 112. In another embodiment, the angles may be unequal and the peak 112 may be positioned closer to one of the outer edges 116 and 118. Although the triangular shaped portion 106 is shown as having substantially straight lines extending from the peak 112, the top of the triangular shaped portion 106 may also be formed using concave, convex, or other lines that are not straight. Optionally, "triangular shaped" may be further defined to include first and second vertical sides (not shown) proximate the outer edges 116 and 118. In yet another embodiment, the top may include more than one peak.

The thickness 110 at the peak 112 or top of the triangle may be at least partially based on the attenuation properties of the material used to fabricate the attenuation filter 100. In one embodiment, the thickness 110 of the peak, or other thickest portion of the attenuation filter 100, may be between three and four millimeters thicker than a thickness at the outer edges 116 and 118 or a thinnest portion of the attenuation filter 100 along the y-z plane 76. The attenuation filter 100 may be formed of aluminum. In some embodiments, the attenuation filter 100 may include portion(s) formed of graphite. In other embodiments, the attenuation filter 100 may include portion(s) formed of an aluminum alloy. In yet other embodiments, the attenuation filter 100 may be at least partially formed of copper. Other materials and combinations of materials may be used to adjust the attenuation along the y-z plane 76. In some embodiments, the attenuation filter 100 may be formed using a molding process, but is not so limited.

For ease of installation, the triangular shaped portion 106, as well as the entire attenuation filter 100, may physically be rectangular in shape an indicated on FIG. 3 with dotted line 127. To provide the triangular shaped attenuation along the y-z plane 76, the consistency of an x-ray attenuating material increases when moving from the outer edges 116 and 118 towards the peak 112. In one example, areas 128 and 129 may be formed of material that has a low or minimal level of x-ray attenuation. Therefore, x-rays that pass through a central portion 122 of the attenuation filter 100 are attenuated to a greater degree or have a higher attenuation coefficient compared to x-rays that pass through outer portions 124 and 126 of the attenuation filter 100. Although shown as thicknesses 110, 114, 115, 119 and 120, it should be understood that the thickness represents x-ray attenuation such that a relatively thicker thickness represents greater attenuation of x-ray (e.g. higher attenuation coefficient) and a relatively thinner thickness represents less attenuation of x-ray (e.g. lower attenuation coefficient).

In yet another embodiment, the triangular shaped portion 106 may be replaced with a convexly curved portion 113 (partially indicated by a dotted line) or other continuously or non-continuously curved portion that does not have a peak 112 but that does approximate a triangular shape. The curved portion is configured to provide greater attenuation within the central portion 122 along the x-axis 52, corresponding to the overlapping region 46, and relatively less attenuation within the outer portions 124 and 126, corresponding to the non-overlapping regions 48 and 50.

Figure 4:
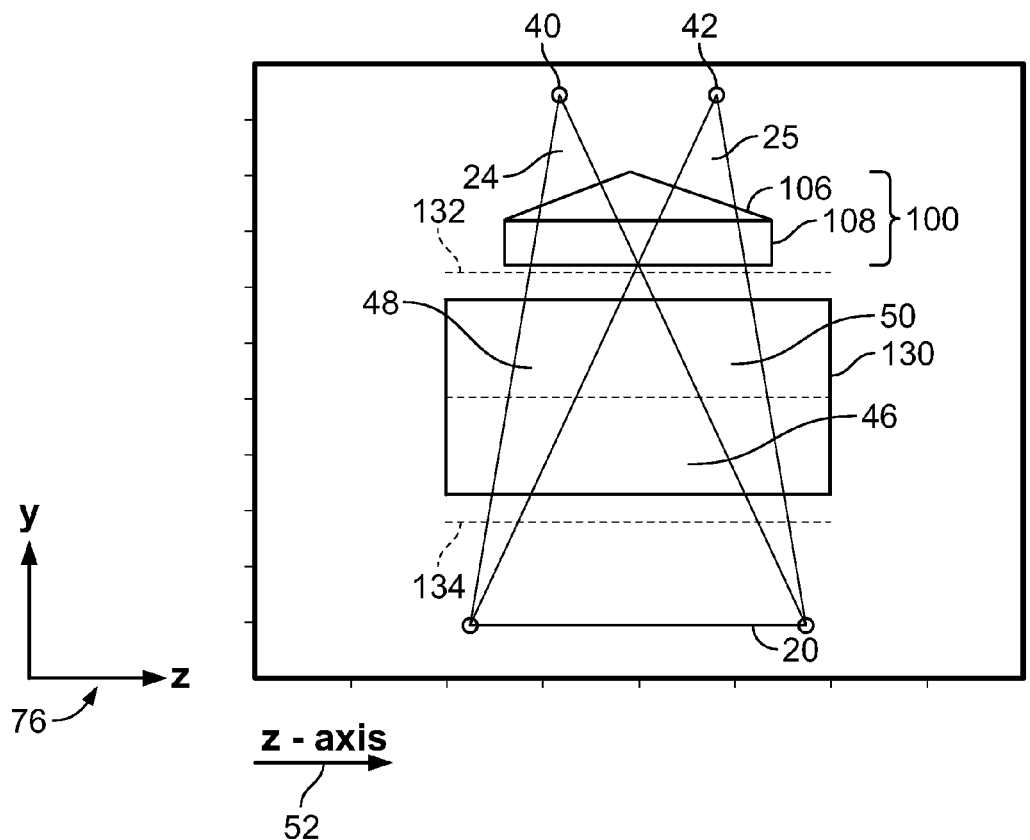
FIG. 4 is a drawing illustrating the attenuation filter centrally positioned between adjacent x-ray sources or anodes and an imaging area in accordance with an embodiment of the present invention.

FIG. 4 illustrates a drawing showing the attenuation filter 100 centrally positioned between the adjacent x-ray sources or anodes 40 and 42 and imaging area 130. The attenuation filter 100 is viewed along the y-z plane 76. Although not shown, a collimator may also be positioned between the anodes 40 and 42 and the imaging area 130. Lines 132 and 134 indicate edges of the bore within the gantry 14 (as shown in FIG. 1) through which the subject 26 is advanced. The detector assembly 20 is positioned opposite the anodes 40 and 42 on an opposite side of the imaging area 130.

The x-ray tube 18 (of FIG. 1) that contains the anodes 40 and 42 may be mounted within a casing (not shown) wherein the x-ray tube 18 and the casing both have an x-ray transmissive window constructed from an x-ray transmissive material such as beryllium, aluminum or titanium. X-rays emitted from the x-ray tube 18 pass through the x-ray tube window and the x-ray tube casing window. In some embodiments, the attenuation filter 100 may be deposited, formed directly onto or otherwise attached to the x-ray tube casing window. In other embodiments, the attenuation filter 100 may be positioned proximate the x-ray tube casing window. Optionally, the attenuation filter 100 may be interconnected with the collimator or a collimator housing.

Although conceptually indicated as the triangular and rectangular shaped portions 106 and 108, it should be understood that the attenuation filter 100 may be integrated into a single filter or piece. Optionally, the triangular and rectangular shaped portions 106 and 108 may be separate pieces that are aligned with respect to each other. Alternatively, the triangular and rectangular shaped portions 106 and 108 may be securely held within a housing (not shown).

The first and second x-ray beams 24 and 25 are transmitted alternately, forming the overlapping region 46 and the non-overlapping regions 48 and 50 within the imaging area 130. The attenuation filter 100 varies the amount of attenuation along the z-axis 52, increasing the attenuation of x-rays transmitted through the overlapping region 46 as compared to the attenuation of x-rays transmitted through the non-overlapping regions 48 and 50.

Figure 5:
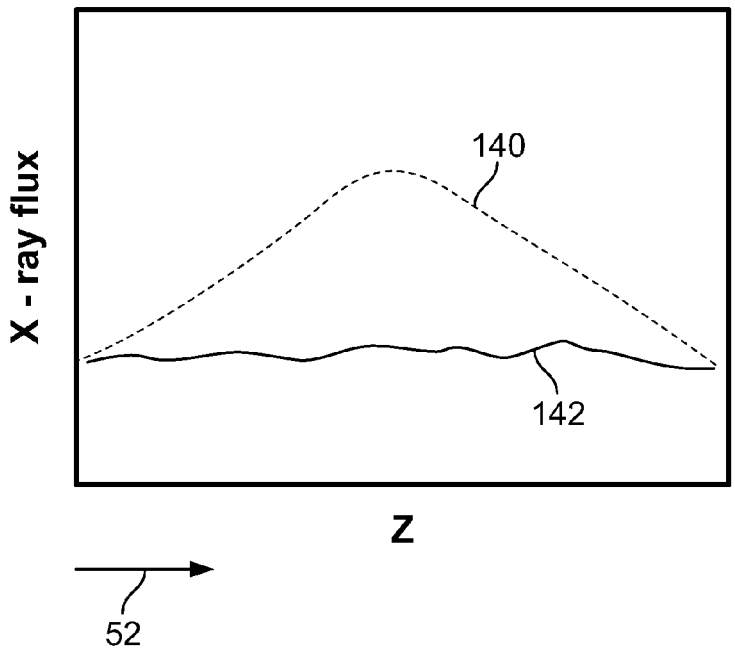
FIG. 5 is a graph illustrating a comparison in the level of x-ray flux along the z-axis of combined images acquired using different x-ray beam attenuation filters in accordance with an embodiment of the present invention.

FIG. 5 illustrates a comparison in the level of x-ray flux along the z-axis 52 of combined images acquired using different x-ray beam attenuation filters. Line 140 indicates the level of x-ray flux along the z-axis 52 using an attenuation filter that does not provide different x-ray attenuation along the z-axis 52. Line 142 indicates the level of x-ray flux along the z-axis 52 using the attenuation filter 100 of FIG. 4 that provides the substantially triangular shaped x-ray attenuation along the z-axis 52. Line 140 indicates increased x-ray flux corresponding to the overlapping region 46, while line 142 illustrates that the increased level of x-ray attenuation within the overlapping region 48 results in an x-ray flux level that is substantially equalized across the combined image. Therefore, the amount of radiation the subject 26 receives is constant across the coverage along the z-axis 52.

Figure 6:
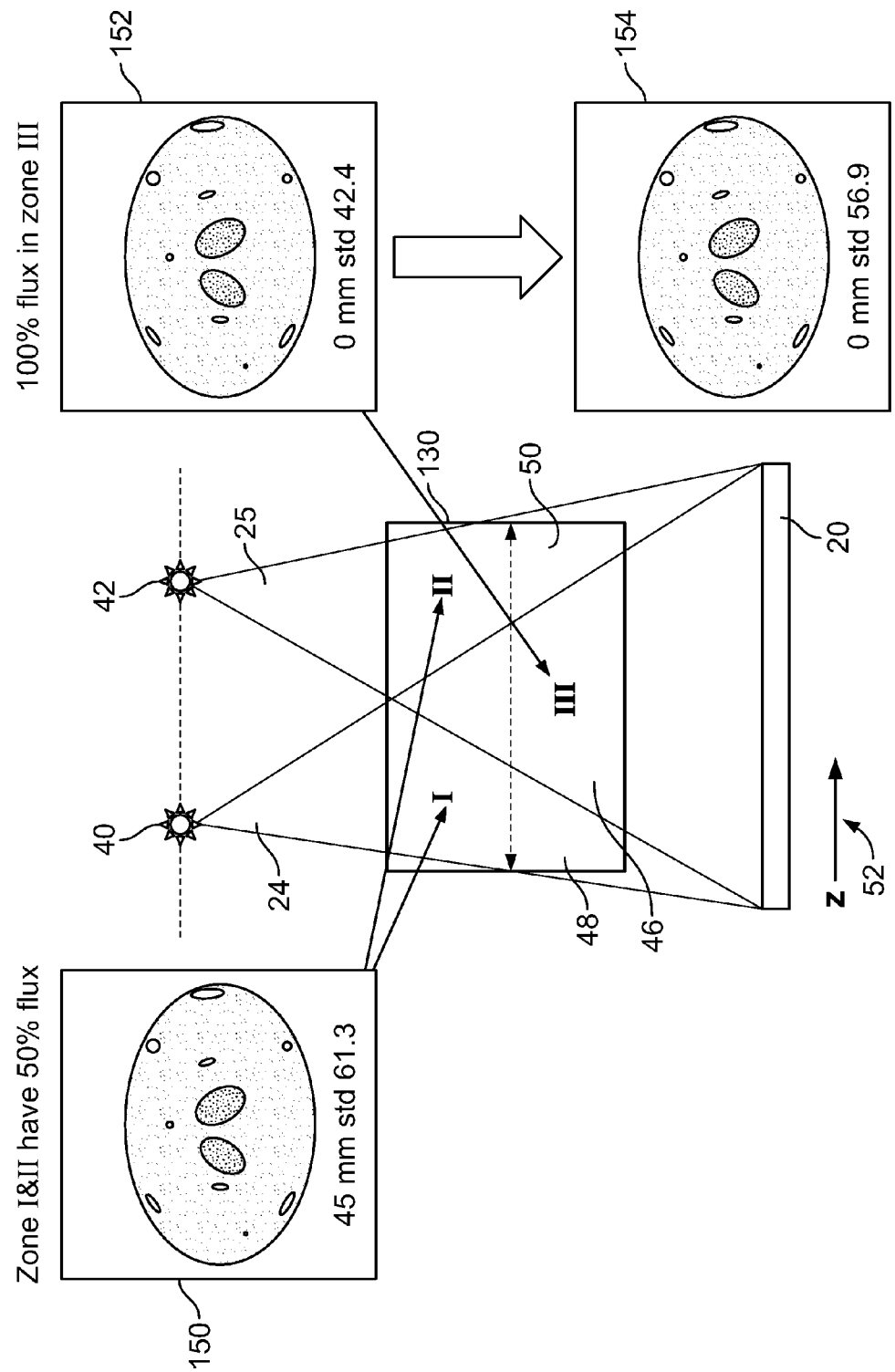
FIG. 6 illustrates exemplary noise measurements in accordance with an embodiment of the present invention.

FIG. 6 illustrates exemplary noise measurements in accordance with an embodiment of the present invention. Again, two x-ray sources or anodes 40 and 42 are illustrated. The non-overlapping regions 48 and 50 of the x-ray beams 24 and 25 within the imaging area 130 are indicated as zones I and II respectively, while the overlapping region 46 is indicated as zone III.

First and second images 150 and 152 represent image data that was acquired using constant x-ray attenuation along the z-axis 52. Portions of the first image 150 that represent image data from within either of the zones I and II (non-overlapping regions 48 and 50) that receive half or fifty percent of the flux as compared to zone III (overlapping region 46) have a noise level of 61.3 Hounsfield Units (HU). Portions of the second image 152 that represent image data from within the zone III have a noise level of 42.4 HU. Therefore, the noise level of the first image 150 is about 44 percent higher than the noise level of the second image 152.

Third image 154 represents image data that was acquired using the attenuation filter 100 of FIG. 4. The portion of the third image 154 that represents the zone III, or overlapping region 46, has a noise level of 56.9 HU. Therefore, the percentage in difference between the noise level of the first image 150 (non-overlapping regions 48 and 50) and the third image 154 (overlapping region 46) is reduced to about 7.7 percent, which is much lower than the 44 percent difference between the first and second images 150 and 152.

Figure 7:
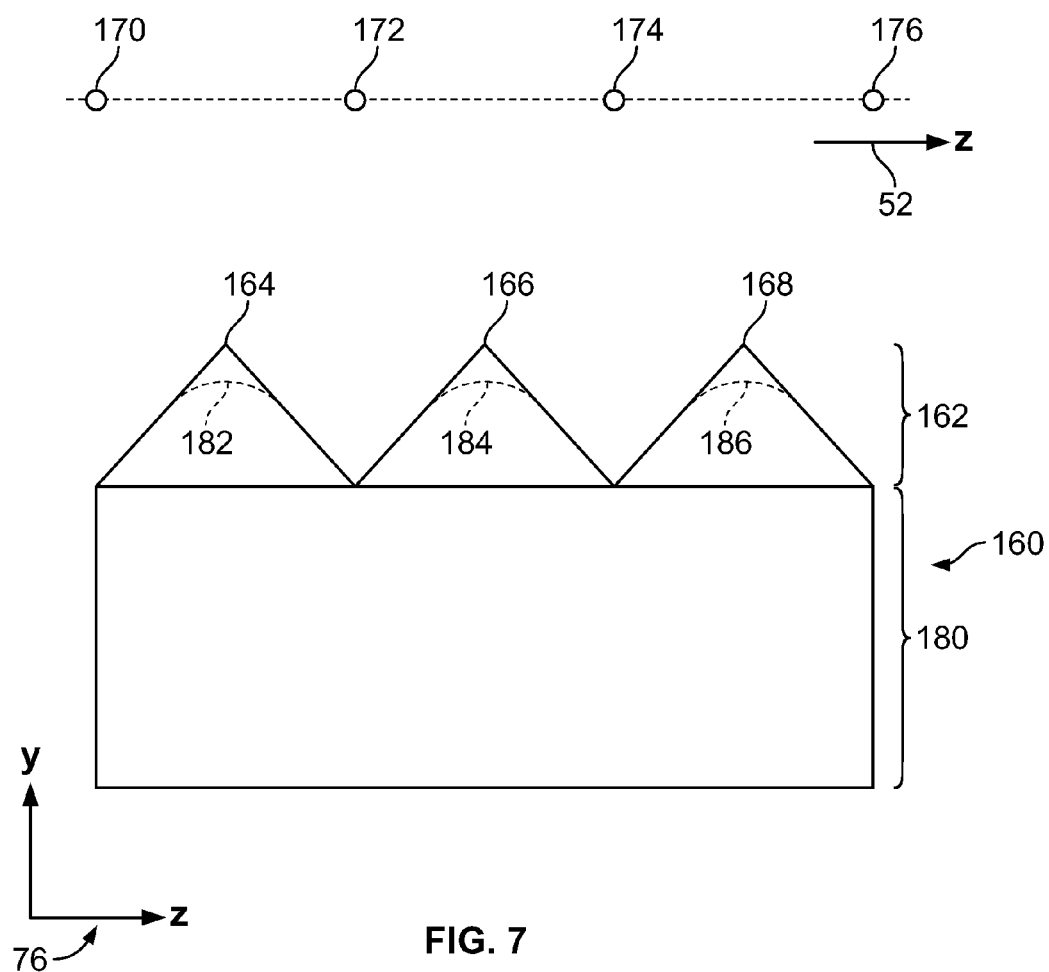
FIG. 7 is a side view of an alternative attenuation filter formed in accordance with an embodiment of the present invention.

FIG. 7 illustrates a side view of an alternative attenuation filter 160 formed in accordance with an embodiment of the present invention. Triangular shaped portion 162 may have more than one peak, such as first, second and third peaks 164, 166 and 168, and may also be referred to as having a jig-saw shape. In one embodiment, the attenuation filter 160 may also have a rectangular shaped portion 180 that provides a constant level of x-ray attenuation, the "U" shaped x-ray attenuation, or other varying level(s) of x-ray attenuation within the x-y plane 74 while providing a constant level of x-ray attenuation along the z-axis 52.

For example, the attenuation filter 160 may be used with an imaging system that has four different sources 170, 172, 174 and 176 displaced along the z-axis 52, wherein the sources 170 and 172 form an overlapping region (not shown), sources 172 and 174 form a different overlapping region, and sources 174 and 176 form yet another different overlapping region. The number of peaks 164-168 may vary based on the number of sources 170-176. As discussed with respect to FIG. 3, in another embodiment, the peaks 164-168 may be replaced by convexly curved portions 182, 184 and 186 or other curved portions that provide greater x-ray attenuation within the overlapping regions and relatively less x-ray attenuation within non-overlapping regions.

A technical effect of at least one embodiment is the ability to combine images that have been acquired using alternating sources that form an overlapping region while minimizing the noise variation across the combined image and minimizing the radiation exposure to the subject. An attenuation filter provides a greater degree of x-ray attenuation within the overlapping region along the z-axis compared to non-overlapping regions. The attenuation filter may provide attenuation in a triangular shape along the z-axis or y-z plane, wherein the peak of the triangle is located within a central portion of the filter along the y-z plane. Therefore, within the y-z plane x-rays that pass through a central portion of the attenuation filter are attenuated to a greater degree compared to x-rays that pass through outer portions of the attenuation filter.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An imaging system comprising:
at least two x-ray sources displaced along a z-axis, the at least two x-ray sources configured to alternately emit x-ray beams;
an x-ray detector assembly configured to detect the x-ray beams; and
an attenuation filter mounted proximate the at least two x-ray sources, the attenuation filter configured to provide different amounts of x-ray attenuation to the x-ray beams along the z-axis.

2. The imaging system of claim 1, wherein the attenuation filter comprises at least one of a substantially triangular shaped portion and a curved portion along the z-axis.

3. The imaging system of claim 1, wherein the attenuation filter provides a greater amount of x-ray attenuation to the x-ray beams proximate a central portion of the attenuation filter along the z-axis and a relatively lesser amount of x-ray attenuation to the x-ray beams proximate outer portions of the attenuation filter along the z-axis.

4. The imaging system of claim 1, wherein the attenuation filter comprises a triangular shaped portion along the z-axis, and wherein a peak of the triangular shaped portion provides greater x-ray attenuation than non-peak portions.

5. The imaging system of claim 1, wherein the attenuation filter comprises one of a triangular shaped portion and a convexly curved portion along a y-z plane and a "U" shaped portion along an x-y plane.

6. The imaging system of claim 1, wherein the x-ray beams partially overlap each other to form an overlapping region within an imaging area, the attenuation filter further configured to provide greater x-ray attenuation within the overlapping region.

7. The imaging system of claim 1, further comprising a processor configured to receive image data based on the x-ray beams, the processor further configured to combine the image data to form a combined image.

8. A method for at least partially compensating for increased x-ray flux from multiple x-ray sources mounted along a z-axis, the method comprising:
transmitting x-ray beams alternately from at least two adjacent x-ray sources, the x-ray beams forming an overlapping region within an imaging area; and
positioning an attenuation filter between the at least two adjacent x-ray sources and an x-ray detector assembly, the attenuation filter providing different amounts of x-ray attenuation to the x-ray beams along the z-axis.

9. The method of claim 8, wherein the attenuation filter has a higher attenuation coefficient corresponding to the overlapping region and a lower attenuation coefficient corresponding to non-overlapping regions within the imaging area.

10. The method of claim 8, wherein the attenuation filter comprises a central portion and outer portions with respect to the z-axis, the central portion providing a higher level of x-ray attenuation than the outer portions.

11. The method of claim 8, wherein the amount of x-ray attenuation provided is based on a location of the overlapping region.

12. The method of claim 8, wherein the transmitting further comprises transmitting x-ray beams from two other adjacent x-ray sources, the x-ray beams forming a second overlapping region within the imaging area, the attenuation filter further providing different amounts of x-ray attenuation along the z-axis based on the overlapping region and the second overlapping region.

13. The method of claim 8, wherein the attenuation filter comprises at least one substantially triangular shaped portion along the z-axis that has a peak, and the positioning further comprises positioning the peak along the z-axis between two adjacent x-ray sources.

14. A computed tomography (CT) imaging system comprising:
at least two x-ray sources aligned along a z-axis;
a detector assembly positioned to detect x-rays beams from the at least two x-ray sources, wherein the at least two x-ray sources are configured to alternately emit x-ray beams that partially overlap within an overlapping region of an imaging area, the imaging area located between the at least two x-ray sources and the detector assembly; and
an attenuation filter positioned between the at least two x-ray sources and the imaging area, the attenuation filter configured to provide relatively higher x-ray attenuation along the z-axis corresponding to the overlapping region and relatively lower x-ray attenuation along the z-axis corresponding to at least one non-overlapping region of the imaging area.

15. The system of claim 14, wherein the attenuation filter is configured to attenuate the x-ray beams using a substantially triangular shape along the z-axis, and wherein a peak of the triangular shape provides a greatest level of x-ray attenuation.

16. The system of claim 14, further comprising a computer operationally coupled to the at least two x-ray sources and the detector assembly, wherein the computer is configured to receive projection data associated with each of the x-ray beams from the at least two x-ray sources, the computer further configured to combine the projection data into a combined image.

17. The system of claim 14, wherein the attenuation filter comprises a plurality of triangular shaped portions along the z-axis, each of the plurality of triangular shaped portions having a peak, and wherein the peaks of the triangular shaped portions provide greater x-ray attenuation than non-peak portions.

18. The system of claim 14, wherein the attenuation filter comprises at least one of a triangular shaped portion and a curved portion along a y-z plane and a substantially "U" shaped portion along an x-y plane.

19. The system of claim 14, wherein the attenuation filter comprises at least one of aluminum, aluminum alloy, copper and graphite.

20. The system of claim 14, wherein a thickness at a peak of the attenuation filter along the z-axis is between three and four millimeters greater than thicknesses at outer edges of the attenuation filter.

* * * * *